US009393349B2

(12) United States Patent
Pickford et al.

(10) Patent No.: US 9,393,349 B2
(45) Date of Patent: Jul. 19, 2016

(54) METAL IMPLANTS

(75) Inventors: Martin Edward Lee Pickford, Hants (GB); Andrew Derek Turner, Abingdon (GB)

(73) Assignee: Accentus Medical Limited, Didcot (GB)

( * ) Notice: Subject to any disclaimer, the term of this patent is extended or adjusted under 35 U.S.C. 154(b) by 0 days.

(21) Appl. No.: 12/539,023

(22) Filed: Aug. 11, 2009

(65) Prior Publication Data

US 2010/0036501 A1 Feb. 11, 2010

Related U.S. Application Data

(63) Continuation of application No. 10/501,538, filed as application No. PCT/GB03/01264 on Mar. 25, 2003, now Pat. No. 7,695,522.

(30) Foreign Application Priority Data

Apr. 16, 2002 (GB) .................................. 0208642.9

(51) Int. Cl.
*A61L 27/54* (2006.01)
*C25D 11/26* (2006.01)
*A61F 2/30* (2006.01)
*A61L 27/04* (2006.01)
*A61L 27/30* (2006.01)
*A61L 27/32* (2006.01)
*C25D 11/02* (2006.01)
*A61F 2/32* (2006.01)

(52) U.S. Cl.
CPC .............. *A61L 27/54* (2013.01); *A61F 2/30767* (2013.01); *A61L 27/04* (2013.01); *A61L 27/306* (2013.01); *A61L 27/32* (2013.01); *C25D 11/02* (2013.01); *C25D 11/26* (2013.01); *A61F 2/3094* (2013.01); *A61F 2/32* (2013.01); *A61F 2002/30929* (2013.01); *A61F 2002/30967* (2013.01); *A61F 2310/00017* (2013.01); *A61F 2310/00023* (2013.01); *A61F 2310/00029* (2013.01); *A61F 2310/0052* (2013.01); *A61F 2310/00089* (2013.01); *A61F 2310/00592* (2013.01); *A61F 2310/00598* (2013.01); *A61F 2310/00796* (2013.01); *A61L 2300/104* (2013.01); *A61L 2300/404* (2013.01); *A61L 2420/02* (2013.01); *A61L 2430/02* (2013.01)

(58) Field of Classification Search
CPC ............ A61F 2013/00936; A61F 2013/51095; A61F 2310/00011; A61F 2310/00023; A61F 2310/00113; A61F 2310/0052; A61F 2310/00598; A61F 2007/0261; A61F 2007/0263; A61L 27/54; A61L 2300/104

USPC ........................................................ 623/23.53
See application file for complete search history.

(56) References Cited

U.S. PATENT DOCUMENTS

| | | | |
|---|---|---|---|
| 3,852,045 A * | 12/1974 | Wheeler et al. ............... 428/566 |
| 4,027,393 A | 6/1977 | Ellis et al. |
| 4,263,681 A | 4/1981 | Notton |
| 4,336,617 A | 6/1982 | Shikita et al. |
| 4,476,590 A | 10/1984 | Scales et al. |
| 4,784,160 A | 11/1988 | Szilagyi |
| 4,806,218 A | 2/1989 | Hemminger et al. |
| 4,813,965 A | 3/1989 | Roberts |
| 4,818,572 A | 4/1989 | Shimamune et al. |
| 4,843,965 A | 7/1989 | Merzals |
| 4,846,837 A | 7/1989 | Kurze |
| 4,938,409 A | 7/1990 | Roberts |
| 5,032,129 A | 7/1991 | Kurze et al. |
| 5,132,003 A | 7/1992 | Mitani |
| 5,185,075 A * | 2/1993 | Rosenberg et al. ........... 205/234 |
| 5,211,663 A | 5/1993 | Kovacs et al. |
| 5,211,832 A | 5/1993 | Cooper et al. |
| 5,310,464 A | 5/1994 | Redepenning |
| 5,454,886 A | 10/1995 | Burrell et al. |
| 5,468,562 A | 11/1995 | Farivar et al. |
| 5,478,237 A | 12/1995 | Ishizawa |
| 5,482,731 A | 1/1996 | Vargas-Gutierrez et al. |
| 5,492,763 A | 2/1996 | Barry et al. |
| 5,503,704 A | 4/1996 | Bower et al. |

(Continued)

FOREIGN PATENT DOCUMENTS

AU   731730 B2   4/2001
AU   731732 B2   4/2001

(Continued)

OTHER PUBLICATIONS

Afshar, "Evaluation of electrical breakdown of anodic films on titanium in phosphate-base solutions", 2004.

(Continued)

*Primary Examiner* — Christopher D Prone
(74) *Attorney, Agent, or Firm* — Christensen O'Connor Johnson Kindness PLLC

(57) ABSTRACT

A metal implant for use in a surgical procedure is provided with a surface layer that is integral with the metal substrate, and which incorporates a biocidal material. The surface layer may be grown from the metal substrate, by anodizing, and the biocidal material incorporated in it by ion exchange. Alternatively the layer may be deposited by electroplating, followed by diffusion bonding so as to become integral with the metal substrate. In either case, silver is a suitable biocidal material; and both the release rate and the quantity of biocidal material should be low to avoid toxic effects on body cells. Electropolishing the surface before formation of the surface layer is also beneficial, and this may be achieved by electropolishing.

5 Claims, No Drawings

(56) References Cited

U.S. PATENT DOCUMENTS

| | | |
|---|---|---|
| 5,520,664 A | 5/1996 | Bricault, Jr. et al. |
| 5,612,049 A | 3/1997 | Li et al. |
| 5,695,857 A | 12/1997 | Burrell et al. |
| 5,723,038 A | 3/1998 | Scharnweber et al. |
| 5,753,251 A | 5/1998 | Burrell et al. |
| 5,753,322 A | 5/1998 | Yamaguchi et al. |
| 5,770,255 A | 6/1998 | Burrell et al. |
| 5,833,463 A | 11/1998 | Hurson |
| 5,837,275 A | 11/1998 | Burrell et al. |
| 5,855,612 A | 1/1999 | Ohthuki et al. |
| 5,958,440 A | 9/1999 | Burrell et al. |
| 5,985,308 A | 11/1999 | Burrell et al. |
| 6,017,553 A | 1/2000 | Burrell et al. |
| 6,066,392 A | 5/2000 | Hisamoto et al. |
| 6,113,636 A | 9/2000 | Ogle |
| 6,180,162 B1 | 1/2001 | Shigeru et al. |
| 6,190,407 B1 | 2/2001 | Ogle et al. |
| 6,191,192 B1 | 2/2001 | Monden et al. |
| 6,267,782 B1 | 7/2001 | Ogle et al. |
| 6,322,588 B1 | 11/2001 | Ogle et al. |
| 6,361,567 B1 | 3/2002 | Dearnaley |
| 6,365,220 B1 | 4/2002 | Burrell et al. |
| 6,423,468 B1 | 7/2002 | Hotta et al. |
| 6,482,444 B1 | 11/2002 | Bellantone et al. |
| 6,509,057 B2 | 1/2003 | Shigeru et al. |
| 6,530,951 B1 | 3/2003 | Bates et al. |
| 6,544,288 B2 | 4/2003 | Osaka et al. |
| 6,582,715 B1 | 6/2003 | Barry et al. |
| 6,663,634 B2 | 12/2003 | Ahrens et al. |
| 6,689,170 B1 | 2/2004 | Larsson et al. |
| 6,719,987 B2 | 4/2004 | Burrell et al. |
| 6,866,859 B2 | 3/2005 | Trogolo et al. |
| 6,913,617 B1 | 7/2005 | Reiss |
| 7,029,566 B2 | 4/2006 | Yen |
| 7,048,541 B2 | 5/2006 | Hall et al. |
| 7,192,445 B2 | 3/2007 | Ellingsen et al. |
| 7,270,721 B2 | 9/2007 | Hilfenhaus |
| 7,291,762 B2 | 11/2007 | Flick |
| 7,452,566 B2 | 11/2008 | Sul |
| 7,488,343 B2 | 2/2009 | O'Brien et al. |
| 2002/0099449 A1 | 7/2002 | Speitling |
| 2002/0112729 A1* | 8/2002 | DeVore et al. ......... 128/207.15 |
| 2003/0045941 A1 | 3/2003 | Lewallen |
| 2003/0091612 A1 | 5/2003 | Sabesan |
| 2004/0116551 A1 | 6/2004 | Terry |
| 2004/0121290 A1 | 6/2004 | Minevski et al. |
| 2004/0161473 A1 | 8/2004 | Joshi |
| 2004/0234604 A1 | 11/2004 | Mecking et al. |
| 2004/0236338 A1 | 11/2004 | Hall |
| 2005/0177248 A1 | 8/2005 | Hall |
| 2005/0221259 A1 | 10/2005 | Anderson |
| 2006/0035039 A1 | 2/2006 | Ylitalo et al. |
| 2006/0198903 A1 | 9/2006 | Storey et al. |
| 2007/0051632 A1 | 3/2007 | Sato et al. |
| 2007/0187253 A1 | 8/2007 | Gilbert et al. |
| 2008/0011613 A1 | 1/2008 | Wang |
| 2009/0035722 A1 | 2/2009 | Balasundaram et al. |
| 2009/0093881 A1 | 4/2009 | Bandyopadhyay et al. |
| 2009/0104242 A1 | 4/2009 | Karlinsey |
| 2009/0124984 A1 | 5/2009 | Hanawa |
| 2009/0155335 A1 | 6/2009 | O'Shaughnessey et al. |
| 2009/0164027 A1 | 6/2009 | Zipprich |
| 2009/0198344 A1 | 8/2009 | Prentice et al. |
| 2009/0204213 A1 | 8/2009 | Liao et al. |

FOREIGN PATENT DOCUMENTS

| | | |
|---|---|---|
| BG | 62807 B1 | 8/2000 |
| CA | 2136456 C | 6/1999 |
| EP | 00257923 B1 | 1/1992 |
| EP | 0555004 A1 | 8/1993 |
| EP | 0761182 A3 | 3/1998 |
| EP | 00875146 B1 | 7/2002 |
| EP | 1207220 B1 | 1/2008 |
| GB | 2072514 A | 10/1981 |
| GB | 2073024 A | 10/1981 |
| GB | 2136448 A | 9/1984 |
| JP | 58-167798 A1 | 10/1983 |
| JP | 62-182298 A1 | 8/1987 |
| JP | 10-158889 A1 | 6/1998 |
| JP | 10-168597 A1 | 6/1998 |
| JP | 10-168598 A1 | 6/1998 |
| JP | 11-181596 | 7/1999 |
| JP | 11-181596 A1 | 7/1999 |
| JP | 11-209895 A1 | 8/1999 |
| JP | 11-229186 A1 | 8/1999 |
| JP | 11-236699 A | 8/1999 |
| JP | 11-302570 A1 | 11/1999 |
| JP | 11-343592 A | 12/1999 |
| JP | 2005287985 A | 10/2005 |
| KR | 10-0910064 B1 | 7/2009 |
| RU | 2167526 C2 | 5/2001 |
| SI | 875146 T1 | 12/2002 |
| WO | WO 81/02667 A1 | 10/1981 |
| WO | WO 81/02668 A1 | 10/1981 |
| WO | WO 92/11043 A1 | 7/1992 |
| WO | WO 93/07924 A1 | 4/1993 |
| WO | WO 95/13704 A1 | 5/1995 |
| WO | WO 95/18637 A1 | 7/1995 |
| WO | WO 98/51231 A1 | 11/1998 |
| WO | WO 99/01089 A1 | 1/1999 |
| WO | WO 99/26666 A2 | 6/1999 |
| WO | WO 00/45724 A1 | 8/2000 |
| WO | WO 00/51659 A1 | 9/2000 |
| WO | WO 00/64505 A1 | 11/2000 |
| WO | WO 00/72777 A1 | 12/2000 |
| WO | WO 01/12246 A1 | 2/2001 |
| WO | WO 02/096475 A1 | 12/2002 |
| WO | WO 03/003938 A1 | 1/2003 |
| WO | WO 03/039609 A1 | 5/2003 |
| WO | WO 03/089023 A1 | 10/2003 |
| WO | WO 03/094774 A1 | 11/2003 |
| WO | WO 2004/002543 A1 | 1/2004 |
| WO | WO 2005/087982 A1 | 9/2005 |
| WO | WO 2006/058906 A1 | 6/2006 |
| WO | WO 2006/104644 A2 | 10/2006 |
| WO | WO 2007/050327 A2 | 5/2007 |
| WO | WO 2007/144667 A2 | 12/2007 |
| WO | WO 2008/096160 A2 | 8/2008 |
| WO | WO 2009/044203 A1 | 4/2009 |
| WO | WO 2009/100792 A2 | 8/2009 |
| WO | WO 2009/100792 A3 | 8/2009 |

OTHER PUBLICATIONS

Aladjem, "Review anodic oxidation of titanium and its alloys", 1973.
Aerospace Material Spec. (AMS 2487A), "Anodic treatment of titanium alloys solution pH 12.4 maximum", 1993-2006.
Aerospace Material Spec. (AMS 2488D), "Anodic treatment—titanium and titanium alloys solution pH 13 or higher", 1977-2006.
Chen, "Surface chemistry of TiCl4 on W(100)", 1996.
Chi, "Antibacterial activity of anodized aluminum with deposited silver", 2002.
Disegi, "Anodizing treatments for titanium implants", 1997.
Dunn, "Anodized layers on titanium and titanium alloy orthopedic materials for antimicrobial activity applications", 1992.
Dunn, "Formation and characterization of anodized layers on CP Ti and Ti-6Al-4OV", 1992.
Dunn, "Gentamicin sulfate attachment and release from anodized Ti-6Al-4V orthopedic materials", 2004.
Edwards, "Coating and surface treatment systems for metals", 1997.
Kawashita, "Bonelike apatite formation on anodically oxidized titanium metal in simulated body fluid", 2004.
Khadiri, "Characterization of titanium oxide thin films anodically grown in phosphoric acid", 2004.
Kokubo, "Novel bioactive materials with different mechanical properties", 2003.
Kurze et al., "Application fields of ANOF layers and composites", 1986.
Li et al., "Calcium phosphate formulation within sol-gel prepared titanium in vitro and in vivo", 1993.

(56) References Cited

OTHER PUBLICATIONS

Li et al., "The role of hydrated silica, titania and alumina in inducing apatite on implants", 1994.
Liu, "Surface modification of titanium, titanium alloys, and related materials for biomedical applications", 2004.
Marchenoir, "Study of porous layers formed by anodic oxidation of titanium under high voltage" (French), 1980.
Marchenoir, "Study of porous layers formed by anodic oxidation of titanium under high voltage" (English translation), 1980.
Martini, "Detachment of titanium & fluorhydroxypatite particles", 2003.
Necula, "In vitro antibacterial >activity of porous TiO2-Ag composite layers against methicillin-resistant *Staphylococcus aureus*", 2009.
Olier, "Influence of the preparation conditions of titanium surfaces on the formation of anodic oxide layers" (French), 1980.
Olier, "Influence of the preparation conditions of titanium surfaces on the formation of anodic oxide layers" (English translation), 1980.
Schierholz, "Efficacy of silver-coated medical devices", 1998.
Schreckenbach, "Characterization of anodic spark-converted titanium surfaces for biomedical applications", 1999.
Shirkhanzadeh, "Bioactive delivery systems for the slow release of antibiotics . . . ", 1995.
Shirkhanzadeh, "Nanoporous alkoxy-derived titanium oxide coating", 1998.
Souza, "EIS characterization of Ti anodic oxide porous films formed using modulated potential", 2007.
Suzuki et al., "Surface treatment of titanium (part 4) in vitro biocompatibility of titanium treated by the anodic spark oxidation", 1991.
Takasaki, "Elution of silver ions from A-type zeolite supporting silver ions in aqueous solutions" (Japanese), 1996.
Takasaki, "Elution of silver ions from A-type zeolite supporting silver ions in aqueous solutions" (English translation), 1996.
Tsukada, "Low-temperature electrochemical systhesis of ZrO2 films on zirconium substrates", 1997.
Xie, "Improvement of surface bioactivity on titanium by water and hydrogen plasma immersion ion implantation", 2005.
Yang, "Preparation of bioactive titanium metal via anodic oxidation treatment", 2004.
Yoshinari, "Influence of surface modifications to titanium on antibacterial activity in vitro", 2001.
Yu, "Synthesis and characterization of phoshated meso porous titanium dioxide with photocatalytic activity", 2003.
Yue, "Bioactive titanium metal surfaces with antimicrobial properties prepared by anodic oxidation treatment", 2009.
USPTO Office Action from U.S. Appl. No. 10/501,538, Nov. 16, 2005.
USPTO Office Action from U.S. Appl. No. 10/501,538, May 1, 2006.
USPTO Office Action from U.S. Appl. No. 10/501,538, Sep. 21, 2006.
USPTO Office Action from U.S. Appl. No. 10/501,538, Apr. 12, 2007.
USPTO Office Action from U.S. Appl. No. 10/501,538, Jul. 11, 2007.
USPTO Office Action from U.S. Appl. No. 10/501,538, Oct. 24, 2007.
USPTO Office Action from U.S. Appl. No. 10/501,538, July 28, 2008.
USPTO Office Action from U.S. Appl. No. 10/501,538, Jan. 16, 2009.
USPTO Office Action for U.S. Appl. No. 12/539,028 dated May 7, 2014.
T. Shibata et al., "The effect of temperature on the growth of anodic oxide film on titanium," Corrosion Science, vol. 37, No. 1, pp. 133-144, 1995.
T. Shibata et al., "The effect of film formation conditions on the structure and composition of anodic oxide films on titanium," Corrosion Science, vol. 37, No. 2, pp. 253-270, 1995.
X. Zhu et al., "Anodic oxide films containing Ca and P of titanium biomaterial," Biomaterials, 22 (2001) 2199-2206.
USPTO Office Action for U.S. Appl. No. 12/539,028 dated Mar. 2, 2011.
USPTO Office Action for U.S. Appl. No. 12/539,028 dated Aug. 17, 2011.
USPTO Advisory Action for U.S. Appl. No. 12/539,028 dated Oct. 31, 2011.
USPTO Office Action for U.S. Appl. No. 12/539,028 dated Sep. 27, 2012.
C. Larrson et al., "Bone Response to Surface Modified Titanium Implants: Studies on Electropolished Implants with Different Oxide Thicknesses and Morphology", Biomaterials 1994, vol. 15, No. 13, pp. 1062-1074.
C. Larrson et al., "Bone Response to Surface-Modified Titanium Implants: Studies on the Early Tissue Response to Machined and Electropolished Implants with Different Oxide Thicknesses", Biomaterials 1996, vol. 17, No. 6, pp. 605-616.
USPTO Office Action for U.S. Appl. No. 12/539,028 dated Dec. 21, 2011.

\* cited by examiner

METAL IMPLANTS

CROSS-REFERENCE TO RELATED APPLICATIONS

This application is a continuation of U.S. patent application Ser. No. 10/501,538, entitled "Metal Implants," filed on Jul. 16, 2004, the entire disclosure of which is incorporated herein by reference.

STATEMENT REGARDING FEDERALLY SPONSORED RESEARCH OR DEVELOPMENT

Not applicable.

BACKGROUND OF THE INVENTION

1. Field of the Invention

This invention relates to metal implants for use in surgical procedures, and in particular to the introduction of a biocidal material into such implants to suppress or control infection.

2. Background of the Invention

Various surgical procedures require the use of implants. For example cancerous bone may be removed, in prosthetic surgery, to be replaced by a metal implant. Such an implant may for example be of titanium alloy, which is very strong and relatively light. To ensure a hard-wearing surface the provision of a titanium nitride coating has been suggested. There is furthermore a risk of introducing infection when implanting such metal implants, and it has been suggested that metallic silver might be electroplated onto metal implants, the silver being a biocidal material that can control infection without causing toxic effects to the patient. However such coatings, whether of titanium nitride or silver, may be undercut due to corrosion from body fluids, so that the coating may detach from the implant, which may increase wear and cause tissue damage.

BRIEF SUMMARY OF SOME OF THE PREFERRED EMBODIMENTS

According to the present invention there is provided an implant for use in a surgical procedure, the implant comprising a metal substrate and a surface layer that is integral with the metal substrate, the layer incorporating a biocidal metal deposited from a solution.

The invention also provides a method of producing such an implant.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

DETAILED DESCRIPTION OF THE PREFERRED EMBODIMENTS

Such an integral surface layer may be generated by growing the layer from the metal itself, for example by an anodising process; or alternatively by depositing the layer for example by electroplating, followed by diffusion bonding so that the layer becomes integral with the metal of the implant. Anodising forms an adherent oxide layer, although if it is carried out in phosphoric acid then a phosphate may be formed. Such an adherent phosphate layer may also be modified to form a hydroxyapatite layer, which can stimulate bone growth.

The biocidal material should preferably be effective for at least 6 weeks, preferably for up to 6 months after surgery, and the release rate should be low to avoid toxic effects on body cells. Furthermore the total quantity of biocidal material is preferably also limited to minimize any toxic effects.

It is also desirable if the surface is highly polished before production of the surface layer. This may for example be achieved by electropolishing.

In principle, a range of different metals may be used for the biocidal metal. In particular, if the layer is a metal layer deposited by electroplating then it clearly must be stable to corrosion. Gold, platinum, iridium and palladium would be potentially suitable, although expensive; silver is preferable as it is not particularly soluble in body fluids due to the presence of chloride ions and the low solubility of silver chloride. If the surface layer contains the biocidal metal in ionic form, then a wider range of metals would be possible. In addition to the elements already mentioned, copper, tin, antimony, lead, bismuth and zinc might be used as ions combined into an insoluble matrix for example of metal oxide or metal phosphate. The rate of release would be controlled, in this case, primarily by the strength of the absorption of the metal ions in the matrix.

The metals that may be used to make such prosthetic implants are typically a form of stainless steel, a titanium alloy, or a cobalt/chromium alloy, although zirconium could also be used. The standard alloys for this purpose are titanium 90% with 6% aluminum and 4% vanadium (British standard 7252), or chromium 26.5-30%, molybdenum 4.5-7%, and the remainder cobalt (British standard 7252 part 4).

Preferably the implant is initially polished to provide a very smooth surface. Both stainless steel (chromium/iron/nickel) and cobalt/chromium alloy can be electro-polished using as electrolyte a mixture of phosphoric acid and glycerine, or a mixture of phosphoric acid and sulphuric acid. Titanium alloy can be electro-polished using acetic acid, or a mixture of nitric and hydrofluoric acids. Alternatively the implants might be subjected to a combination of anodic passivation with mechanical polishing, which may be referred to as electrofinishing, this process removing the oxide that protects surface roughness, the surface at that point then being electrochemically re-passivated, so producing a mirror-smooth finish. Various electrolytes are suitable for this purpose, including nitric acid mixed with sulphuric acid, sodium hydroxide, sodium phosphate, or sodium hydroxide mixed with sodium nitrate.

After polishing the surface of the metal, either silver deposition or surface conversion can take place. Considering surface conversion first, a layer of metal oxide or phosphate may be formed by anodising in a suitable electrolyte, so that the oxide or phosphate layer builds out from the surface of the metal. Biocidal metal ions can then be absorbed from an aqueous salt solution into the oxide or phosphate matrix, for example the ions $Ag^+$ or $Cu^{++}$. Cations of palladium, platinum or even ruthenium could be absorbed in a similar way. If desired, deposited silver, platinum or palladium ions could then be converted to metal, or deposited ruthenium ions converted to insoluble $RuO_2$, within the oxide or phosphate surface coating, this reaction being performed chemically or electrochemically or by light.

Considering now silver deposition, the coating should be thin to prevent toxic effects. A high degree of adherence to the underlying metal can be ensured by first removing the surface oxide layer by anodic etching, followed by a brief reversal of polarity in the presence of appropriate ions, so as to cover the surface with a thin coating of silver. This may be repeated to ensure there are no pin-holes. The plating electrolyte may include hydrofluoric acid, or may be an alkaline cyanide electroplating electrolyte. After deposition, the silver coating should be diffusion bonded so as to form an inter-metallic layer, by heating the implant to an elevated temperature. Typically it should be heated to above 800° C., preferably between 810° C. and 950° C., in an inert atmosphere for example of argon for a period of between 1 and 6 hours. This substantially eliminates the risk of coating delamination. However with titanium-based implants the temperature must not exceed 850° C. as titanium would undergo a phase change from alpha to beta form above this temperature.

In place of silver, other metals such as platinum or palladium may be electro-deposited and then thermally treated in a similar fashion so as to form an inter-metallic layer.

The invention will now be further and more particularly described, by way of example only.

A hip implant is made of titanium alloy (Ti/Al/V). The implant is cleaned ultrasonically using first acetone as the liquid phase, and then a 1 M aqueous solution of sodium hydroxide, and is then rinsed in de-ionised water. The cleaned implant is then immersed in a stirred 12 weight % solution of phosphoric acid, and is anodised for 2 hours at a maximum voltage of 10 V and a maximum current of 10 mA/cm$^2$, so as to form a surface coating of titanium phosphate. It is then rinsed in de-ionised water again. The surface, which is initially pale grey, turns to a darker matt grey as a consequence of the anodising, with a slightly yellow hue.

The implant is then immersed in a stirred 0.1 M aqueous solution of silver nitrate, and left for 2 hours. As a result of ion exchange there is consequently some silver phosphate in the titanium phosphate coating. The implant is then ready to be implanted. During exposure to body fluids there will be a slow leaching of silver ions from the phosphate layer, so that any bacteria in the immediate vicinity of the implant are killed. Infection arising from the implant is therefore suppressed.

Experimental samples of this titanium alloy were cleaned, anodised to form a layer of titanium phosphate, and then subjected to ion exchange to form silver phosphate, following the procedure described above. One sample was placed in direct daylight for 110 hours; the exposed surface became darkened as a result of this exposure to daylight, indicating the formation of silver metal by photo-reduction. The other sample was immersed in a solvent containing a mixture of 4 M nitric acid and 0.5 M sodium fluoride (equivalent to hydrofluoric acid) to dissolve the coating. The dark grey surface coating was removed completely within 3 minutes, leaving a silver-grey finish. The resulting solution was analyzed for the presence of silver by atomic absorption spectrometry, and the concentration of silver was found to be equivalent to an average surface loading of 73 μg/cm$^2$.

Although the present invention and its advantages have been described in detail, it should be understood that various changes, substitutions and alterations may be made herein without departing from the spirit and scope of the invention as defined by the appended claims.

What is claimed is:

1. An implant for use in a surgical procedure, the implant comprising:
   a metal substrate; and
   (ii) an anodized surface layer that is integral with the metal substrate and that consists of:
      (a) material selected from a metal oxide, a metal phosphate and a combination thereof; and
      (b) a biocidal metal in ionic form; and
   wherein the biocidal metal in ionic form is releasable over time from the surface layer, wherein the quantity and release of the biocidal metal are such as to kill bacteria in a vicinity of the implant, to minimize toxic effects on body cells, and to be effective in suppressing infection after the surgical procedure.

2. An implant as claimed in claim 1 wherein the surface layer comprises metal phosphate.

3. An implant as claimed in claim 1 wherein the biocidal metal comprises silver.

4. An implant as claimed in claim 1 wherein the biocidal metal is effective in suppressing infection for at least 6 weeks after the surgical procedure.

5. An implant as claimed in claim 1 wherein the metal substrate comprises a titanium alloy consisting essentially of titanium, aluminium and vanadium.

* * * * *